United States Patent [19]

Morelle et al.

[11] Patent Number: 5,066,487
[45] Date of Patent: Nov. 19, 1991

[54] ANTISUDORAL COMPOSITION COMPRISING DIBASIC ALUMINIUM SALTS OF ACYLATED AMINO ACIDS

[75] Inventors: Jean V. Morelle; Eliane Lauzanne-Morelle, both of Paris, France

[73] Assignee: Rhone-Poulenc Chimie, France

[21] Appl. No.: 406,435

[22] Filed: Sep. 12, 1989

[30] Foreign Application Priority Data

Sep. 14, 1988 [FR] France .................. 88 11983

[51] Int. Cl.$^5$ .................. A61K 7/38; C07F 5/06
[52] U.S. Cl. .................. 424/68; 424/81; 556/181
[58] Field of Search .................. 424/68, 81, 78; 556/181

[56] References Cited

FOREIGN PATENT DOCUMENTS 1105939  7/1981  Canada .

OTHER PUBLICATIONS

Chem. Abstracts, vol. 106, entry 182458t.
Chemical Abstracts, 98, entry 56050g.
Chem. Abstracts, 90:28897e.

Primary Examiner—Thurman K. Page
Assistant Examiner—Peter F. Kulkosky
Attorney, Agent, or Firm—Lucas & Just

[57] ABSTRACT

Dibasic aluminium salts of acylated amino acids having the formula

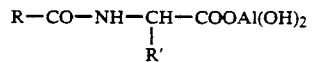

($R=C_5—C_{10}$ hydrocarbon, R' is the main chain of the illustrated α-amino-acid) have antisudoral properties. R' may be such that the α-aminoacid is singular, e.g. lysine, glycine or aspartic acid, or a mixture, e.g. a hydrolysate of a protein such as collagen, keratin or casein. R may be saturated, e.g. pentyl, heptyl or nonyl, or unsaturated, e.g. dec-9-enyl. Antisudoral compositions containing these salts are described.

19 Claims, No Drawings

ANTISUDORAL COMPOSITION COMPRISING DIBASIC ALUMINIUM SALTS OF ACYLATED AMINO ACIDS

The invention relates to antisudoral compounds, to methods for their preparation and to compositions containing them.

It is well known that although many aluminium salts are endowed with antisudoral properties, very few of them can be effectively employed. The more active, such as aluminium chloride and hydroxychloride, e.g. $AlCl_3 6H_2O$, have a number of disadvantages. They are aggressive towards the skin, due to their hydrolysis in contact with water leading to a pH of between 0.5 and 1.5, even when they are dissolved in alcohols. It has been shown in numerous publications that the antisudoral effect of these aluminium chloride derivatives is due to their denaturing action on proteins at the secretory canal level, blocking the canal by acanthosic phenomena (coagulation of albumen). The high hydrochloric acidity and biological interference give rise to intolerance of these aluminium salts, which in turn restricts their use. Compositions, which must contain 20 to 30% of the salts to be active, may only be used for three or four applications per week. If treatment is stopped, the level of sweat secretion reaches that before treatment three or four days after the last application. Thus treatment must be continued indefinitely.

The invention provides aluminium salts of lipo-amino acids having the general formula

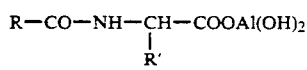

wherein R represents a hydrocarbon chain having from 5 to 10 carbon atoms and R' represents the main chain of the illustrated α-amino acid. This may be a single amino acid, such as glycine, lysine or aspartic acid, or may be a mixture of amino acids, for example from the hydrolysis of proteins such as collagen, keratin or casein.

The compounds according to the invention have been found to be endowed with antisudoral properties. Unlike the aluminium chloride derivatives of the prior art, they are insoluble in water. When dispersed in water, with the use of a wetting agent, the dispersion shows a pH of from 4 to 6, corresponding to that of healthy skin. They do not cause coagulation and denaturing of proteins and do not cause acanthosic phenomena (coagulation of albumen). For these reasons, they do not cause irritation to the user and are well tolerated.

The compounds according to the invention also have an anti-inflammatory action. Under the influence of sweating hypersecretion, the glands secrete many substances, including amino acids. Microorganisms can degrade these to polyamides such as cadaverine and putrescine, derived from lysine and ornithine. This causes inflammation of the intertrigo tissued folds.

The anti-microorganisms properties of the compounds are thus manifested in an anti-inflammatory action.

The antisudoral properties may be tested using the bromophenol blue paper test. This test may be carried out by the user. Experiments with a dozen people showing excess sweating of the soles of the feet and the palms of the hands were carried out for several months, summer and winter, and showed improvement of the condition.

The compounds according to the invention may be prepared by a process which comprises reacting in aqueous solution an alkali metal salt of an acylated amino acid of the formula

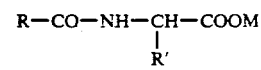

wherein R and R' are as defined in claim 1 and M represents an alkali metal with aluminium sulphate or aluminium chloride, while maintaining the reaction environment at an approximately neutral pH by addition of a base as necessary, and adjusting the pH to between 4 and 5 at the end of the reaction by addition of aluminium sulphate or a mineral acid. If the pH of the reaction medium is not controlled, the release of acid by hydrolysis of the aluminium salt (e.g. sulphuric acid from aluminium sulphate) drives the pH towards 3, resulting in monobasic aluminium salts of the lipo-amino acid (OH structure). These have antisudoral activities 50% less than the dibasic salts of $(OH)_2$, structure. The adjustment of the pH at the end of the reaction, after precipitation of the insoluble dibasic salt, may be effected using a dilute solution of aluminium sulphate, corresponding to 10% of the quantity used in the reaction proper, or using a dilute mineral acid such as 20% hydrochloric acid.

The preferred compounds according to the invention are those in which the acylating group R is pentyl, heptyl, nonyl and dec-9-enyl. These give the following acylated aluminium salts of amino acids.

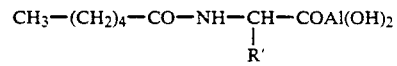

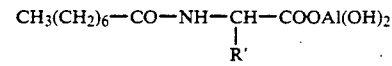

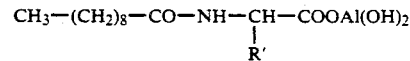

and

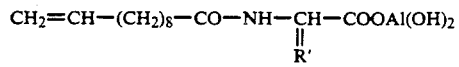

in which the acylating group is respectively caproyl, caprylyl, nonanoyl and undecylenoyl.

These long chain acids lead to salts containing an average aluminium content of about 10%, ensuring good antisudoral activity. The maximum aluminium content is obtained when R has 5 carbon atoms and R'=H, that is when glycine is the amino acid, whilst the minimum aluminium content is obtained when R has 10 carbon atoms and the amino acid is a protein hydrolysis mixture which typically has a mean molecular weight of about 120.

The following examples, in which all percentages are by weight, illustrate the invention.

EXAMPLE 1

Preparation of Aluminium Dihydroxy Undecylenoylcollagenate 200 g of undecylenoylcollagenic acid was neutralised with 100 ml of a 30% soda solution (pH 10.9) forming a sodium undecylenoylcollagenate solution. 232 g of crystalline aluminium sulphate was dissolved in 1500 ml of water and added to the sodium undecylenoylcollagenate solution. The pH was monitored, and further soda solution was added to maintain the pH at approximately 7. At the end of the reaction, when precipitation was complete, the pH was adjusted to between 4 and 5 by addition of an excess of a 10% solution of crystalline aluminium sulphate or by addition of 85 ml of 20% hydrochloric acid. The product was separated by filtration, washed and dried.

EXAMPLE 2

A preparation in the form of a cream for tubes comprises

| | |
|---|---|
| Aluminium Dihydroxy Caprylylglycinate | 5% |
| Palmitostearate of Glycerol | 5% |
| Polyethylenoxylated Fatty alcohols | 10% |
| Stearine | 5% |
| Propylene Glycol | 10% |
| Water to | 100% |

Alternatively the aluminium dihydroxy caprylylglycinate may be replaced by

| | |
|---|---|
| Aluminium Dihydroxy Undecylenoylcollagenate | 7% |
| or Aluminium Dihydroxy Caproylcollagenate | 5% |
| or Aluminium Dihydroxy Caprylylkeratinate | 8% |

EXAMPLE 3

A preparation in the form of a fluid emulsion for applicators comprises

| | |
|---|---|
| Aluminium Dihydroxy Caprylylaspartate | 7% |
| Polyethylenoxylated Cetyl Alcohol | 8% |
| Dioctyl sulphosuccinate | 1% |
| Water to | 100% |

Alternatively the aluminium dihydroxy caprylylaspartate may be replaced by

| | |
|---|---|
| Aluminium Dihydroxy Undecylenoylglycinate | 6% |
| or Aluminium Dihydroxy Caprylylcollagenate | 5% |

EXAMPLE 4

A preparation in the form of a gel of tubes or applicators comprises

| | |
|---|---|
| Aluminium Dihydroxy Caprylyllysinate | 5% |
| Ethanol | 45% |
| Carboxyvinyl Polymer | 2% |
| Diethanolamine | 2% |
| Water to | 100% |

Alternatively the aluminium dihydroxy caprylyllysinate may be replaced by

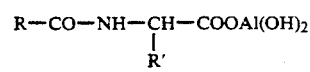

We claim:

1. An antisudoral composition containing a dibasic aluminium salt of an acylated amino acid having the formula $$R-CO-NH-CH(R')-COOAl(OH)_2$$

wherein R represents a hydrocarbon chain having from 5 to 10 carbon atoms and R' represents the main chain of the illustrated α-amino acid or a mixture of such salts, together with a diluent or carrier.

2. An antisudoral composition according to claim 1 in which the dibasic aluminium salt of the acylated amino acid, or the mixture of such salts, comprises from 5 to 10% of the composition.

3. An antisudoral composition comprising

| | |
|---|---|
| aluminium dihydroxy caprylylglycinate | 5% |
| palmitostearate of glycerol | 5% |
| polyethylenoxylated fatty alcohol | 10% |
| stearine | 5% |
| propylene glycol | 10% |
| water to | 100% |

4. An antisudoral composition comprising

| | |
|---|---|
| aluminium dihydroxy undecylenoylcollagenate | 7% |
| palmitostearate of glycerol | 5% |
| polyethylenoxylated fatty alcohol | 10% |
| stearine | 5% |
| propylene glycol | 10% |
| water to | 100% |

5. An antisudoral composition comprising

| | |
|---|---|
| aluminium dihydroxy caproylcollagenate | 5% |
| palmitostearate of glycerol | 5% |
| polyethylenoxylated fatty alcohol | 10% |
| stearine | 5% |
| propylene glycol | 10% |
| water to | 100% |

6. An antisudoral composition comprising

| | |
|---|---|
| aluminium dihydroxy caprylylkeratinate | 8% |
| palmitostearate of glycerol | 5% |
| polyethylenoxylated fatty alcohol | 10% |
| stearine | 5% |
| propylene glycol | 10% |
| water to | 100% |

7. An antisudoral composition comprising

| | |
|---|---|
| aluminium dihydroxy caprylylaspartate | 7% |
| polyethylenoxylated cetyl alcohol | 8% |
| dioctyl sulfosuccinate | 1% |
| water to | 100% |

8. An antisudoral composition comprising

| | |
|---|---|
| aluminium dihydroxy undecylenoylglycinate | 6% |

-continued

| polyethylenoxylated cetyl alcohol | 8% |
| --- | --- |
| dioctyl sulfosuccinate | 1% |
| water to | 100% |

9. An antisudoral composition comprising

| aluminium dihydroxy caprylylcollagenate | 5% |
| --- | --- |
| polyethylenoxylated cetyl alcohol | 8% |
| dioctyl sulfosuccinate | 1% |
| water to | 100% |

10. An antisudoral composition comprising

| aluminium dihydroxy caprylyllysinate | 5% |
| --- | --- |
| ethanol | 45% |
| carboxyvinyl polymer | 2% |
| diethanolamine | 2% |
| water to | 100% |

11. An antisudoral composition comprising

| aluminium dihydroxy undecylenoylcollagenate | 7% |
| --- | --- |
| ethanol | 45% |
| carboxyvinyl polymer | 2% |
| diethanolamine | 2% |
| water to | 100% |

12. A method for the treatment of sudoration, the method comprising topically applying a composition according to claim 10 to the patient.

13. An antisudoral composition according to claim 1 in which R represents a radical selected from the group consisting of pentyl, heptyl, nonyl and dec-9-enyl.

14. An antisudoral composition according to claim 1 in which R' is such that the α-amino acid is selected from the group consisting of lysine, glycine and asparatic acid.

15. An antisudoral composition according to claim 13 in which R' is such that the α-amino acid is selected from the group consisting of lysine, glycine and aspartic acid.

16. An antisudoral composition according to claim 1 in which R' is such that the αamino acid is a protein hydrolysis mixture.

17. An antisudoral composition according to claim 16 in which the protein is selected from the group consisting of collagen, keratin and casein.

18. An antisudoral composition according to claim 13 in which R' is such that the α-amino acid is a protein hydrolysis mixture.

19. An antisudoral composition according to claim 18 in which the protein is selected from the group consisting of collagen, keratin and casein.

* * * * *

UNITED STATES PATENT AND TRADEMARK OFFICE
CERTIFICATE OF CORRECTION

PATENT NO. : 5,066,487
DATED : November 19, 1991
INVENTOR(S) : Jean V. Morelle et al.

It is certified that error appears in the above-identified patent and that said Letters Patent is hereby corrected as shown below:

Column 2, line 52, delete the formula and substitute therefor the following formula:

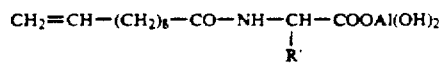

Column 6, lines 13-14, change "asparatic" to --aspartic--.

Column 6, line 20, change "αamino" to --α-amino--.

Signed and Sealed this

Twenty-fifth Day of May, 1993

Attest:

MICHAEL K. KIRK

Attesting Officer     Acting Commissioner of Patents and Trademarks